| United States Patent [19] | [11] | 4,161,481 |
|---|---|---|
| Priemer et al. | [45] | Jul. 17, 1979 |

[54] PROCESS FOR THE ISOLATION OF PURIFIED ANTHRAQUINONE

[75] Inventors: Joachim Priemer, Odenthal; Georg Nicklas; Nikolaus Schulz, both of Cologne, all of Fed. Rep. of Germany

[73] Assignee: Bayer Aktiengesellschaft, Leverkusen, Fed. Rep. of Germany

[21] Appl. No.: 852,123

[22] Filed: Nov. 16, 1977

[30] Foreign Application Priority Data

Dec. 4, 1976 [DE] Fed. Rep. of Germany ....... 2655103

[51] Int. Cl.$^2$ ............................................. C07C 49/68
[52] U.S. Cl. ................................................... 260/369
[58] Field of Search ................................ 260/369, 706

[56] References Cited

U.S. PATENT DOCUMENTS

| 1,464,844 | 8/1923 | Downs | 260/369 |
|---|---|---|---|
| 1,591,712 | 7/1926 | Lewis | 260/369 |
| 1,701,186 | 2/1929 | Lewis | 260/369 |
| 1,845,281 | 2/1932 | Jaeger | 260/369 |
| 2,852,517 | 9/1958 | Lynn | 260/706 |
| 2,938,913 | 5/1960 | Weyker et al. | 260/369 |
| 3,113,140 | 12/1963 | Matz et al. | 260/369 |
| 3,441,574 | 4/1969 | Morgan et al. | 260/369 |
| 3,870,730 | 3/1975 | Scharfe et al. | 260/369 |

FOREIGN PATENT DOCUMENTS 1175453  11/1958  France ...................................... 260/369

Primary Examiner—Allen B. Curtis
Assistant Examiner—Raymond Covington
Attorney, Agent, or Firm—Sprung, Felfe, Horn, Lynch & Kramer

[57] ABSTRACT

A process has now been found for the isolation of purified anthraquinone from the crude anthraquinone which has been obtained by oxidation of naphthalene to give naphthoquinone, reaction of the oxidation product with butadiene to give tetrahydroanthraquinone, oxydehydrogenation of this reaction product with molecular oxygen to give a crude anthraquinone and optionally removal of naphthalene, phthalic anhydride and low-boiling substances from this crude anthraquinone, which is characterized in that the crude anthraquinone is treated with an oxygen compound of the elements of the first and/or second main group of the periodic system at an elevated temperature, optionally in the presence of a solvent, and purified anthraquinone is then isolated by subliming the anthraquinone present at a temperature of about 190° to about 290° C. and a pressure of about 1 to about 90 mm Hg and then desubliming it under the same pressure, or by vaporizing the pretreated anthraquinone at a temperature of about 290° to about 380° C. and a pressure of about 90 to about 760 mm Hg and condensing the vapor under a pressure of about 90 to about 760 mm Hg.

8 Claims, No Drawings

PROCESS FOR THE ISOLATION OF PURIFIED ANTHRAQUINONE

The present invention relates to a process for the isolation of purified anthraquinone from crude anthraquinone by treating the crude anthraquinone with an oxygen compound of the elements of the first and/or second main group of the periodic system, and to the separation of the anthraquinone from high-boiling residues by sublimation or vaporisation with subsequent desublimation or condensation, respectively.

It is known to purify anthraquinone which has been prepared, for example, by chromic acid oxidation or air oxidation of anthracene, by crystallisation, for example from nitrobenzene, or by sublimation (Ullmann's Enzyklopadie der technischen Chemie (Ullmann's Encyclopaedia of Industrial Chemistry), 4th edition, volume 7, page 581, 583).

However, these methods are not applicable in the case of crude anthraquinone obtained, for example, in accordance with DT-OS (German Published Specification) No. 2,245,555, which is prepared by oxidation of naphthalene to naphthoquinone, reaction of naphthoquinone with butadiene to give tetrahydroanthraquinone and oxy-dehydrogenation of tetrahydroanthraquinone to give anthraquinone, and which is produced as a sump product, since the high-boiling impurities, which cause a strong discoloration, possess a solubility similar to that of anthraquinone and thus cannot be removed by simple crystallisation. On the other hand, some of the compounds constituting the impurity are volatile, so that purification of the anthraquinone, for example by simple distillation or sublimation, is technically very involved and is associated with high losses of anthraquinone.

A process has now been found for the isolation of purified anthraquinone from the crude anthraquinone which has been obtained by oxidation of naphthalene to give naphthoquinone, reaction of the oxidation product with butadiene to give tetrahydroanthraquinone, oxy-dehydrogenation of this reaction product with molecular oxygen to give a crude anthraquinone and optionally removal of naphthalene, phthalic anhydride and low-boiling substances from this crude anthraquinone, which is characterised in that the crude anthraquinone is treated with an oxygen compound of the elements of the first and/or second main group of the periodic system at an elevated temperature, optionally in the presence of a solvent, and purified anthraquinone is then isolated by subliming the anthraquinone present at a temperature of about 190° to about 290° C. and a pressure of about 1 to about 90 mm Hg and then desubliming it under the same pressure, or by vaporising the pretreated anthraquinone at a temperature of about 290° to about 380° C. and a pressure of about 90 to about 760 mm Hg and condensing the vapour under a pressure of about 90 to about 760 mm Hg.

It is possible to employ, in the process according to the invention, for example, a crude anthraquinone which has been obtained in accordance with DT-OS (German Published Specification) No. 2,245,555 and which has been prepared by oxidation of naphthalene to give naphthoquinone, reaction of naphthoquinone with butadiene to give tetrahydroanthraquinone and oxy-dehydrogenation of tetrahydroanthraquinone to give anthraquinone. In such cases, the content of high-boiling residues in the crude anthraquinone can be approximately 20 to 50% by weight. High-boiling residues are understood as compounds which have boiling points above 380° C., for example 9,10-dihydroxy-naphthacenequinone and monohydroxy-naphthacenequinone.

In accordance with the process of the invention it is necessary, for separating off and isolating purified anthraquinone by sublimation or vaporisation with subsequent desublimation or condensation, respectively, from the crude anthraquinone obtained in accordance with processes of DT-OS (German Published Specification) No. 2,245,555, to pretreat the crude anthraquinone with oxygen compounds of the elements of the first and/or second main group of the periodic system at elevated temperature, for example at about 150° to about 400° C., preferably about 200° to 350° C., optionally in the presence of an organic solvent which is inert under these conditions, for example ethylene glycol, cyclohexanol, phenol or cresol.

Examples of suitable oxygen compounds of the elements of the first and second main group of the periodic system are the oxides, hydroxides, carbonates, bicarbonates and carboxylates of lithium, sodium, potassium, magnesium, calcium, strontium and barium. A single of said oxygen compounds or mixtures of said oxygen compounds can, of course, be used. The oxides and/or hydroxides of the metals of the first and second main group of the periodic system are particularly suitable, sodium hydroxide, calcium hydroxide and/or calcium oxide being employed preferentially.

Depending on the content of impurities in the crude anthraquinone, the said oxygen compounds can be employed, for example, in quantities of about 0.1 to 20% by weight, in particular 1 to 10% by weight, relative to the crude anthraquinone to be purified.

Depending on the reaction temperature applied and the extent of mixing, the treatment times can be, for example, between a few minutes and several hours. In general, treatment times of about 5 minutes to about 1 hour are adequate.

The treatment of the crude anthraquinone with the abovementioned oxygen compounds is customarily carried out under normal pressure, but can also be carried out under reduced or elevated pressure.

The heat treatment of the crude anthraquinone with the oxygen compounds of the elements of the first and/or second main group of the periodic system can be carried out discontinuously or continuously in suitable mixing or reaction apparatuses. Examples of suitable mixing or reaction apparatuses are screw machines and kneading machines, all-phase reaction apparatuses being employed preferentially. All the apparatuses to be used must be capable of being heated, for example to temperatures of about 400° C., and they should make possible a definite residence time, for example residence times of up to 2 hours, and ensure as narrow as possible a spectrum of residence times and good intermixing of the reactants. In addition, the apparatuses should be of heavy construction, since the product becomes pasty to viscous after the treatment has been effected.

The process according to the invention can be carried out by introducing the crude anthraquinone to be purified into the reaction apparatus in the liquid form. For this purpose it is necessary to heat the crude anthraquinone, for example to about 290° to about 330° C. In carrying out the process according to the invention continuously, the oxygen compounds of the elements of the first and/or second main group of the periodic system, for example sodium hydroxide or a mixture of sodium hydroxide and calcium oxide or calcium hydroxide, can be metered in continuously, in a solid, pulverulent form, separated from the liquid crude anthraquinone feed, laterally into the reaction apparatus via a screw, and it is particularly advantageous if the oxygen compounds are introduced by means of a twin metering screw which is, for example, self-cleaning and which reaches to the internal wall of the reaction apparatus, and the oxygen compounds of the elements of the first and/or second main group of the periodic system, after leaving the screw flights, are immediately picked up by mixing devices and are intermixed. The temperature of the feed screw is preferably at all places below the melting point or softening point of the oxygen compounds of the elements of the first and/or second main group of the periodic system, that is to say is at about 20° to 310° C.

A product which consists of purified anthraquinone and a residue which is no longer sublimable is obtained in accordance with the procedure described above.

The separation and isolation of purified anthraquinone from the pretreated crude anthraquinone can, in accordance with the process according to the invention, be carried out, for example, in accordance with one of the two following variants:

Variant 1:

Purification by means of a sublimation procedure with subsequent desublimation.

Variant 2:

Purification by means of a vaporisation procedure with subsequent condensation.

The two variants will be illustrated in greater detail in the following text.

Variant 1 (compare Diagram 1)

The viscous to pasty crude anthraquinone leaving the reaction apparatus for the treatment with the oxygen compounds of the first and/or second main group of the periodic system is cooled by means of coolers which are suitable for this purpose, for example to temperatures of about 250° to 280° C. Suitable coolers are all apparatuses which can be employed for contact drying or cooling and which are capable of processing, that is to say of converting into a granular form, the feed product, which is still viscous and which, on cooling, passes into the solid phase, without the cooling surfaces gumming up or the product blocking the apparatus in large lumps. All horizontal, preferably cylindrical or slightly conical vessels with strong mixing devices which are self-cleaning and which can, in addition, also be constructed as cooling surfaces, are, for example, suitable for this task.

If an apparatus which allows grains of a diameter of more than 10 mm to be formed is used for cooling and solidifying the product, a grinding device which causes the feed product not to exceed a maximum particle size before being fed into the subsequent sublimation apparatus, for example a disc drier, must be connected downstream of the cooler. Mills which can be employed are, inter alia, hammer mills equipped with sieves and without sieves, beater mills and, in addition, all types of crushing rolls, roll mills and the like.

The particle size of the product to be employed for the sublimation should not exceed about 10 mm. Surprisingly, it has been found that below a particle size of about 10 mm, the particle size has no effect on the efficiency of the sublimation apparatus.

The comminuted product is fed into a contact drier, preferably a disc drier, which operates under a vacuum, via lock systems which are customary in industry, for example the arrangement slide valve — vessel — slide valve. The disc drier can be of conventional construction, but the external walls should, in addition, be capable of being heated. The heat for the sublimation procedure can be fed to the product through the heated discs, which are preferably heated with heat transfer oil. The subliming vapours of anthraquinone are passed through a filter in which entrained fine-grain particles are retained. Filters which can be used are all tube filters and plate filters or similar filters with any desired technical arrangement for purifying the filter medium (for example mechanical beating and vibrating; or compressed air impulse), which are capable of being heated. All the filters must be constructed so as to be vacuum-tight. The filter materials, for example filter tubes, must be able to withstand the high temperatures for a long time, as well as the mechanical stress during cleaning. In addition to the filter systems described above, electrostatic filters are also suitable.

Downstream of the dust filter, the anthraquinone vapours are desublimed, preferably under vacuum, onto suitable machines, such as scraped coolers, screw machines or desublimers. It is advantageous to evacuate the disc drier via the filter and the desublimer.

It is also possible to convey the product to be sublimed as a liquid into a suitable sublimer via a vacuum lock. Sublimers which can be employed are screws of the most diverse construction, and also vessels having mixing and kneading devices or all-phase apparatuses.

Subsequent grinding and cooling of the sublimate which has been isolated makes it possible to put it in bins. The sublimate consists of purified anthraquinone. Between the cooling apparatus and the bin there must be a vacuum lock. The non-sublimable residue in the disc drier can be discharged from the disc drier via a discharging device, for example an output screw and a lock system and can subsequently be cooled under nitrogen blanketting.

Sublimation in accordance with variant 1 is generally carried out under a pressure of about 1 to about 90 mm Hg, preferably about 5 to about 30 mm Hg. The temperature which is necessary for the sublimation is about 190° to about 290° C., preferably about 220° to 260° C. In order to reach this temperature in the sublimation apparatus, it is necessary to heat the apparatus to a temperature of about 210° to about 320° C., preferably to about 240° to 300° C.

The desublimation of the anthraquinone vapours takes place at a temperature, on the cooling walls, of about −50° to about 260° C., preferably at about 20° to 100° C. The pressure here is about 1 to 90 mm Hg, preferably about 5 to 30 mm Hg.

The anthraquinone obtained in accordance with variant 1 generally has a degree of purity higher than 99.8%. The yield is approximately 95% of theory.

Variant 2 (compare Diagram 2)

The viscous to pasty crude anthraquinone leaving the reaction apparatus for the treatment with the oxygen compounds of the first and/or second main group of the periodic system is fed to a vaporisation apparatus, which operates under vacuum, via a suitable vacuum lock, for example an output screw. Vaporisation apparatuses can, for example, be vaporiser screws of the most diverse construction; twin-screw conveyors with self-operating cleaning of the shafts are preferably employed. Vaporisers of a horizontal, cylindrical construction having built-in stirring, mixing and kneading devices, or all-phase driers can also be used.

The vaporisation of the anthraquinone from the anthraquinone residue mixture is effected from the liquid phase. After the vaporisation of the anthraquinone has been effected, a residue in a solid form remains on the screw outlet or, generally speaking, the vaporiser outlet, and this is discharged into a vacuum lock system, for example via an output screw. The residue is cooled in customary cooling apparatuses under nitrogen blanketing.

The vaporisation of the anthraquinone to be purified in accordance with variant 2 is customarily carried out under a pressure of about 90 to about 760 mm Hg, preferably about 90 to 230 mm Hg. In the course thereof, the temperature in the vaporisation apparatus should be in the range from about 290° to about 380° C., preferably about 290° to 320° C. The vaporisation apparatus is generally heated from the outside by means of heat transfer oils.

The condensation is carried out, for example, at a temperature of about −50° to 250° C., advantageously at about 20° to 100° C. The pressure during the condensation should be about 90 to 760 mm Hg, preferably about 90 to 230 mm Hg.

The anthraquinone obtained in accordance with variant 2 generally has a degree of purity higher than 99%. The yield is 95% of theory.

The purified anthraquinone obtained by means of the process according to the invention can be employed direct for nitration to give mononitroanthraquinones or dinitroanthraquinones, which are valuable intermediate products for anthraquinone dyestuffs (compare, for example, DT-OS (German Published Specification) No. 2,232,464).

Both the process routes described will be illustrated in greater detail by means of one example each, without, however, limiting the process according to the invention to the said examples.

EXAMPLE 1

The heat treatment of crude anthraquinone with calcium oxide and sodium hydroxide was carried out continuously in an all-phase reactor. The crude anthraquinone contained approximately 35% by weight of residues; phthalic anhydride was below the limit of detection of less than 0.1%.

The crude anthraquinone was fed into the apparatus from above at a rate of 10 kg/hour of liquid. 0.5 kg/hour of calcium oxide and 0.05 kg/hour of sodium hydroxide were conjointly metered, in a pulverulent form, via a twin metering screw, laterally into the all-phase reactor, into the first of three sections. The speed of rotation of the working shaft was varied between 15 and 40 revolutions per minute. The residence time was approximately 0.5 to 1.5 hours. The product temperature was approximately 310° C. The product leaving the all-phase reactor was viscous to pasty. With only slight cooling or admission of cold air, pure anthraquinone sublimed out of the treated product, in the form of pale yellow crystals. The viscous product was collected in vessels, cooled and then ground to a particle size of less than 3 mm with a beater mill having a mesh insert. This product was now sublimed discontinuously at a feed rate of 0.6 kg per bath on a disc drier with a disc area of 0.1 m$^2$, at 10 mm Hg and a product temperature of 245° C. and a heating agent temperature of 300° to 310° C. The vapours were purified from entrained dust in a tube filter and were then desublimed in a scraped cooler cooled with water. The resulting anthraquinone had a purity of 99.8%. During all the periods of test, the residue was dry and free-flowing. Caking on the disc drier and the transporting devices was not observed.

The yield of pure anthraquinone was 95% of theory.

EXAMPLE 2

The crude anthraquinone, treated as in Example 1, was cooled and ground subsequently to the alkali treatment. This treated and ground product has first to be re-melted, because of the spatial separation of the alkali treatment and the vaporiser screw. The melting temperature was 286° C. The molten product was fed into the vaporiser screw. The pressure in the vaporiser screw was 130 mm Hg; the product temperature was between 300° and 340° C. Vaporisation was also carried out for a period at 100 mm Hg and a product temperature of 290° to 320° C. The throughput was 3 to 7 kg of crude anthraquinone per hour. The anthraquinone vapours were passed through a filter and were then condensed in a cooling coil. Pure anthraquinone was discharged in a solid form at the outlet of the cooling coil. The non-vaporisable residue was produced in a solid phase at the outlet of the vaporiser screw.

The resulting anthraquinone had a purity of 99.3%. The yield was 95% of theory.

EXAMPLE 3

The crude anthraquinone treated, cooled and ground as in Example 1 was melted at normal pressure in a heated screw machine and then continuously fed in liquid to pasty form into a sublimator via a vacuum lock screw. The sublimater consisted of an allphase apparatus suitable for continuous operation which had an effective volume of 12 liters and a heating area of 1 m$^2$. The dust containing anthraquinone vapours were passed through a heated tube filter which was made out of heat resisting material and had a filtering area of 0.84 m$^2$. Thereby the dust was separated. The cleaning of the tube filter was effected by pressure impulses of nitrogen in intervals of 6 minutes whereby the pressure of nitrogen was 1 to 2 bar and each impulse had a durance of 1/10 sec.. The dust which was obtained in the filter was removed via a buffer system equipped with locking armatures followed by cooling in a nitrogen atmosphere. The residue obtained in the sublimator was removed in a dry pulverized form and cooled. The purified anthraquinone vapours flowed into a desublimator which was cooled with water and equipped with a rotating cooler having a cooling area of 0.43 m$^2$. The inert gas coming in through leckages and the filter cleaning procedure was removed by suction through a filter (filtering area 0.43 m$^2$) of the same construction and mode of operation as described above. The described pure anthraquinone was removed at the exit of the desublimator via a discharging valve. The pressure in the sublimator was 30 to 40 mbar, the product temperature was about 260° C. and the temperature of the heating medium was 310° C. The pressure in the desublimator was some mbar lower than in the sublimator due to pressure lost in the filter. The product temperature at the exit of the desublimator was between 30° to 80° C. (depending from the rate of flow). The temperature of the discharged inert gas was close to the product temperature. The flow rate of crude anthraquinone was up to 35 kg per hour corresponding to 20 to 25 kg per hour of discharged pure anthraquinone. The discharged anthraquinone had a purity of more than 99.3%. The bulk weight was between 0.5 and 0.6 kg per liter.

Diagram 1

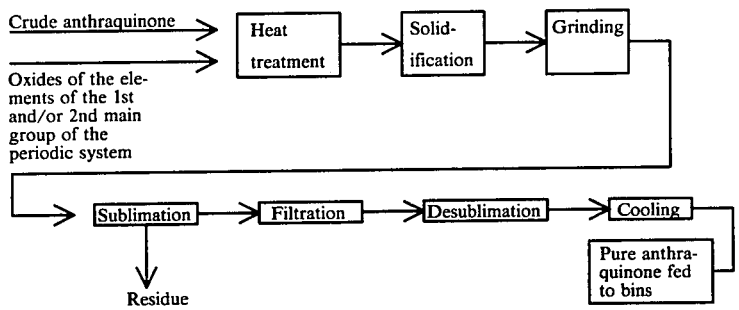

Diagram 2

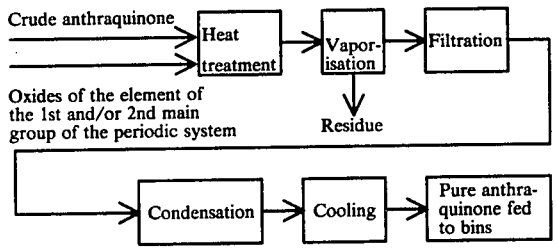

What is claimed is:

1. Process for the isolation of purified anthraquinone from crude anthraquinone which has been obtained by oxidation of naphthalene to give naphthoquinone, reaction of the oxidation product with butadiene to give tetrahydroanthraquinone, oxy-dehydrogenation of the reaction product with molecular oxygen to give a crude anthraquinone and optionally removal of naphthalene, phthalic anhydride and low-boiling substances from this crude anthraquinone, which comprises treating said crude anthraquinone with an oxygen compound of the elements of the first and/or second main group of the Periodic System in solid, pulverulent form and in an amount of 0.1 to 20% by weight relative to said crude anthraquinone at an elevated temperature, optionally in the presence of an organic solvent, and then isolating purified anthraquinone by subliming the pretreated anthraquinone in the presence of said oxygen compound at a temperature of about 190° to about 290° C. and a pressure of about 1 to about 90 mm Hg and then desubliming it under the same pressure, or by vaporizing the pretreated anthraquinone at a temperature of about 290° to about 380° C. and a pressure of about 90 to about 760 mm Hg and condensing the vapour under a pressure of about 90 to about 760 mm Hg.

2. Process according to claim 1, wherein the treatment of the crude anthraquinone with the oxygen compound is carried out at about 150° to 400° C.

3. Process according to claim 1, wherein the treatment of the crude anthraquinone with the oxygen compounds of the elements of the first and/or second main group of the periodic system is carried out in a reactor equipped with mixing or kneading devices, the oxygen compounds being fed into the reactor laterally in a solid, pulverulent form and the feed device reaching into the reaction space almost to the mixing and kneading devices.

4. Process according to claim 1, wherein the ground, pretreated crude anthraquinone is sublimed in a contact drier.

5. Process according to claim 1, wherein the pretreated crude anthraquinone is fed to a sublimer in the liquid phase.

6. Process according to claim 1, wherein the sublimation is carried out at a temperature of about 220° to 260° C. and a pressure of about 5 to 30 mm Hg.

7. Process according to claim 1, wherein the anthraquinone vapours are desublimed in a desublimer under a pressure of about 5 to 30 mm Hg.

8. Process according to claim 1, wherein the pretreated crude anthraquinone is vaporized at a temperature of about 290° to 320° C. and a pressure of about 90 to 230 mm Hg.

* * * * *